United States Patent [19]
Chun et al.

[11] Patent Number: 6,140,060
[45] Date of Patent: Oct. 31, 2000

[54] CLONED LYSOPHATIDIC ACID RECEPTORS

[76] Inventors: Jerold J. M. Chun, 5747 Baja Mar, La Jolla, Calif. 92037-7705; Jonathan H. Hecht, 9188 Regents Rd., Apt. D, La Jolla, Calif. 92037-1443

[21] Appl. No.: 08/763,938

[22] Filed: Dec. 12, 1996

[51] Int. Cl.[7] ............ C12N 15/63; C12N 15/00; C12N 5/00
[52] U.S. Cl. .......... 435/7.1; 435/320.1; 435/325; 435/455; 435/69.1; 536/23.5; 536/24.31
[58] Field of Search ............... 536/23.5, 24.31; 435/320.1, 325, 172.3, 69.1, 7, 4, 6, 7.1, 455

[56] References Cited

FOREIGN PATENT DOCUMENTS

96/39436  12/1996  WIPO .

OTHER PUBLICATIONS

GenBank Database Sequence for bases 1–1436 from Brain Res. Mol. Brain Res. 42 (2), 245–254 (1996).
GenBank Database Sequence for bases 1552 from Brain Res. Mol. Brain Res. 42 (2), 245–254 (1996).
Hecht et al., Journal of Cell Biology, vol. 135, pp. 1071–1083, Nov. 1996.
Hecht et al., Society of Neuroscience Abstracts, vol. 21, p. 1289, Abstract No. 511.6, Nov. 1995.
Saeki et al., FEBS Letters, vol. 336, pp. 317–322, Dec. 27, 1993.
Macrae et al., Molecular Brain Research, vol. 42, pp. 245–254, 1996.
Masana et al., Receptor and Channels, vol. 3, pp. 255–262, 1995.

*Primary Examiner*—Jasmine Chambers
*Assistant Examiner*—Jill D. Martin
*Attorney, Agent, or Firm*—Arent Fox Kintner Plotkin Kahn

[57] ABSTRACT

Described herein is an isolated polynucleotide encoding an LPA receptor. Also described is a recombinant DNA molecule comprising a nucleic acid encoding an LPA receptor and expression controlling elements linked therewith, as well as the use of nucleic acid coding for an LPA receptor for expression to obtain a functional receptor protein and for further gene cloning to identify structurally related receptor proteins. Also described herein is LPA receptor as a product of recombinant production in a cellular host. Described is a method of utilizing the LPA receptor in a chemical screening program to identify LPA receptor ligands. The invention further describes antibodies directed to the LPA receptor for use for example in diagnosis of conditions wherein the levels of LPA are altered.

22 Claims, 2 Drawing Sheets

```
   1 GAATTCGGCA CGAGGCACAG TGCTGCCCTC CGTAGGCTCC GGGTTGTGCT GGGGTGAGGC
  61 TTGGGTTGGG TTGGCCCGGC ACTGGCGTGA ACTGCGGAGC TGGACCTAGC AGGCTTACAG
 121 TTCCTCCTAG CATGACCGAG ATCTGATCAG CCAACCCGCG CATTGCTTTT TGTGCTGGC
 181 ACTGCAGTGC AGGGGGCCTC TTCATGCCCC CAAACTACAG CACTGTCATC GCAGCTGCCT
 241 CTACTTCCAG CCCTGTAATT TCACAGCCCC AGTTCACAGC CATGAACGAA CAACAGTGCT
 301 TCTACAATGA GTCTATCGCC TTCTTTTATA ACCGGAGTGG GAAATATCTA GCCACAGAAT
 361 GGAACACAGT GAGCAAGCTG GTGATGGGAC TGGGCATCAC TGTTTGCGTG TTCATCATGT
 421 TGGCCAATCT CCTGGTCATG GTGGCAATCT AGTCAACCG CCGCTTCCAT TTCCCTATTT
 481 ATTACTTGAT GCCAACCTG GCTGCTGCAG ACTTCTTGC TGGATTGGCC TACTTCTACC
 541 TGATGTTCAA TACAGGACCT AATACCCGGA GACTGACTGT TAGCACGTGG CTCCTCCGGC
 601 AGGGCCTCAT TGACACCAGC CTGACAGCTT CTGTGGCCAA CCTGCTGGCT ATTGCTATCG
 661 AGAGGCACAT CACGGTTTTC CGCATGCAGC TCCATACACG AATGAGCAAC CGGGCGGTGG
 721 TGGTGGTGAT TGTAGTCATC TGGACTATGG CCATTGTGAT GGGTGCTATA CCCAGTGTGG
 781 GCTGAACTG CATCTGTGAT ATCGATCACT GTTCCAACAT GGCACCCCTC TACAGTGACT
 841 CCTACTTAGT CTTCTGGGCC ATTTTCAACC TGGTGACCTT TGTGGTCATG GTGGTTCTCT
 901 ACGCTCACAT CTTTGGCTAT GTTCGCCAGA GACTATGAG GATGTCTCGG CATAGTTCTG
 961 GACCCAGGAG GAATCGGGAC ACCATGGGAT GGTCTCTTGT ATTGCTGGAT GTGTGCTGCC
1021 GTGCCTTTAT TGTCTGCTGG ACTCCTGGCC TATGAGAAGT TCTTCCTCCT CCTGGCCGAG TTCAACTCTG
1081 CGCAGTGCGA TGTCCTGGCC TATGAACCC CATCATCTAC TCCTACGCG ACAAAGAGAT GAGCGCCACC TTCAGGCAGA
1141 CTATGAACCC CATCATCTAC TCCTACGCG AGAACCCTA ATGGCCCCAC GAAGGCTCT GACCGCTCG
1200 TCCTGTGTTG CCAGCGCAAC GAGAACCACC ATTCTGGCTG GAGTTCACAG CAAGCGACCAC TCTGTGGTTT
1261 CCTCCTCCCT CAACCACACC AGCCGGCCT CTGTGATCT GTGAACCCCA CCCTACCCCC CATTGCCAGG
1321 AGAAGGAAGC CAGCCGACTG GAGCCAGAGG AGATGAGGAC ACTCCTGTAC TTAACACTAA CCAATGGCAG
1381 GCAAGGTGGG GAGCCAGCCAAG TAGACCCAAG AGACTTGAGG ATGAATTTAT TTGGCAGGCC CCATCTCTC
1441 TATTTGTCCC TAGACCCAAG AGACTTGAGG ATGAATTTAT GTGGAATTGA GAAATGGACT CTGGGGTGAC
1501 CTTTGGAAAA CAGAAGGGGA CCGTCTGTG GTGGAATTGA ATTTTATGTG GTTTGGCTTA AGCCAGGAAA
1561 CGTGTAGCAT TCACTAACTA GACTTAAAAG TATACAATCG AGTATACACA GGCTTCCCT TTAAAGAACA
1621 AAAAAATCTG CTGAATTGAG TATACAATCG AGTATACACA GGCTTCCCT TTAAAGAACA
1681 AACAATACAT TGCATTTATT AATGAGTATG TTTATGCCTG ACAGCATGTT TGTGATCGAA
1741 AAGACTGCTA AACTGACATA GATGAGTTGT TTTTTTT TTGTTTTTG TTTTTTTTA
1801 CATGATGGAG GAAAAGTATA AATTAGAATG ATTTTTGTGT TTGTTTAGAA AGCAAGCATG
1861 TGGTGTGTGT ATTCAGTATG CCTTTCTTTA AGATAAAAG GCCACTATTT TAAATCTCT
1921 AGGGAATAGA AGAATCTAGT AAAAACCAGT ATTCATTTAG GCTACAGGAA AAACCATATC
1981 CTAATCAATT ACCTTTTAAT TAAAGTAATG AAATATACAT GAAAGGCAAA GTAATGTGAG
2041 CTTGTCACCC AAAGAGTGTG TGCTCTCCAA ACGCTGGAGG AGATGAAGCT GTAGCGTTGT
2101 CCCTGCATAG TGAAGATACC CACGTGCGTT CTCAGTGCCA GACCCTCAGT GGGACTTGTT
2161 TTAAAGCCTG TGGTTTCCA AGTTAGAAAA TAATACCTAC TTACTATAGA AACTTGAAA
2221 ATTGCAGAAC TGTGTGAAAA AAAAAAAAA
```

SEQ. ID No. 1

100  |L A Y F Y L| M F N T G P N T R R L T V S T |W L L R Q G L I D T S L|  TM III

133  |T A S V A N L L A I A I| E R H I T V F R M Q L H T R M |S N R R V V|  TM IV

166  |V V I V V I W T M A I V M G A I P| S V G W N C I C D I D H C S N M

199  A P L Y S D |S Y L V F W A I F N L V T F V V M V V L| Y A H I F G Y  TM V

232  V R Q R T M R M S R H S S G P R R N R D T M M S L |L K T V V I V L|  TM VI

265  |G A F I V C W T P G L V L L L L| D V C C P Q C D V |L A Y E K F F L|  TM VII

298  |L L A E F N S A M N P I I| Y S Y R D K E M  S A T F R Q I L C C Q R

331  N E N P N G P T E G S D R S A S S L N H T I L A G V H S N D H S V V

SEQ. ID No. 2

FIG. 2

CLONED LYSOPHOSPHATIDIC ACID RECEPTORS

FIELD OF THE INVENTION

The invention is in the field of molecular biology. It relates, more particularly, to clones lysophosphatidic receptors and their use in drug screening and related applications.

BACKGROUND TO THE INVENTION

Lysophosphatidic acid, LPA, is a phospholipid signalling molecule that has a wide variety of effects on many different cell types (Moolenaar, 1995, Curr. Opin. Cell Biol. 7:203–210), including neuronal cells. Possible functions of LPA in cortical neurogenesis, based on known bioactivities of LPA and biological events occurring within the ventricular zone of the cerebral cortex, include regulation of cytoskeletal events such as interkinetic nuclear movement, cell rounding, and cleavage plane orientation, mitogenesis, gap junction regulation and influence on the binding and assembly of fibronectin which is expressed in the embryonic cortex. Additionally, regulation of apoptosis, recently shown to occur in the vz may also be influenced by LPA signalling. Further, recent evidence implicates LPA in the proliferation of certain cancer cells (Xu et al. 1995, J. Cell Physiol. 163:441–450).

Although LPA is believed to act through a G-protein coupled receptor (GPCR), a cDNA clone of this receptor has not been identified, in part reflecting the chemical characteristics of LPA that result in unacceptably high levels of non-specific binding, making techniques such as expression cloning impractical for discovery of this receptor.

SUMMARY OF THE INVENTION

The LPA receptor has now been cloned and characterized. Accordingly, the present invention provides an isolated polynucleotide encoding a LPA receptor. In aspects of the invention, nucleic acid coding for LPA receptor is utilised for expression to obtain functional receptor protein and for further gene cloning to identify structurally related receptor proteins. In related aspects of the invention, anti-sense versions of LPA receptor-encoding nucleic acids and fragments thereof are obtained and utilised to regulate LPA receptor expression.

In another of its aspects, LPA receptor is provided as a product of recombinant product in a cellular host. In related aspects, there are provided recombinant host cells that express LPA receptor, as well as receptor-bearing membranes derived from such cells, and expression constructs in which nucleic acid coding for the LPA receptor is linked to expression controls functional in the selected host cell.

In another of its aspects, the LPA receptor is utilised in a chemical screening program to identify LPA receptor ligands. This method comprises the steps of incubating the candidate ligand with an LPA receptor-producing cell of the present invention, or with a membrane preparation derived therefrom, and then assessing the interaction by determining receptor/candidate ligand binding.

In another of its aspects, the invention provides antibodies directed to the LPA receptor, for use for example in diagnosis of conditions wherein the levels of LPA receptor are altered.

BRIEF DESCRIPTION OF THE DRAWINGS

FIG. 1 shows SEQ ID NO: 1.

FIG. 2 shows SEQ ID NO: 2.

DETAILED DESCRIPTION AND PREFERRED EMBODIMENTS

The invention relates in one respect to polynucleotides that code for lysophosphatidic acid (LPA) receptors, Such polynucleotides may be in the form of RNA, or in the form of DNA including cDNA, genomic DNA and synthetic DNA. The LPA receptors are characterized by structural features common to the G-protein coupled receptor class, including seven transmembrane regions, and by the functional properties of binding LPA and, when expressed functionally in a host cell, responding to LPA binding by signal transduction.

The activity of G-protein coupled receptor such as a LPA receptor may be measured using any of a variety of appropriate functional assays in which activation of the receptor results in an observable change in the level of some second messenger system, such as adenylate cyclase, calcium mobilization, inositol phospholipid hydrolysis or guanylyl cyclase. Alternatively, cell proliferation, actin-based cytoskeletal changes, Rho/Rac/$Cd_e$ 42 activation, serum response stimulation or transcription of certain genes may be measured.

In one embodiment of the invention, the LPA receptor is encoded by the nucleic acid sequence of SEQ ID NO. 1. This particular LPA receptor-encoding nucleic acid, also referred to as the vzg-1 gene, is a cDNA of murine origin and encodes an LPA receptor characterized structurally as a single 364 amino acid (41 kD) polypeptide chain of SEQ ID NO 2. With respect to structural domains of this LPA receptor, hydropathy analysis reveals seven putative transmembrane domains, one spanning residues 47–70 inclusive (TM I), another spanning residues 80–105(TM II), a third spanning residues 121–144 (TM III), a fourth spanning residues 160–182(TM IV), a fifth spanning residues 205–224 (TM V), a sixth spanning residues 256–280 (TM VI) and a seventh spanning residues 290–310 (TM VII).

In one embodiment the invention provides LPA encoding nucleic acids, or fragments thereof, as a tools useful to identify structurally related nucleic acids. At low stringency hybridization conditions, for instance, nucleic acid libraries can be probed to identify genes that are at least about 40% homologous to vzg-1. Obviously, if the homolog from a particular species is sought e.g. human, the appropriate library should be probed. To facilitate isolation of LPA receptor encoding homologs of vzg-1 , homologs desirably have 80% sequence identity at the nucleic acid level to vzg-1. More desirably they are 90% identical, and most desirably they have at least 95% sequence identity when compared to vzg-1. It will be clear that increasing the stringency of the hybridization conditions will result increased sequence identity of the homolog thereby isolated, with vzg-1. In order to isolate LPA receptor encoding homologs of vzg-1 it is desirable but not essential to screen libraries of brain origin; fetal brain libraries are particularly suitable sources, including fetal cortical libraries. Therefore, the invention includes not only vzg-1 but structural homologs and particularly those that code for proteins having LPA receptor properties. Thus, the invention provides nucleic acids that encode LPA receptors, including murine LPA receptor and mammalian homologs thereof as well as synthetic variants of these. Synthetically derived variants of the LPA receptor include LPA binding variants that incorporate one or more, e.g. 1–10, amino acid substitutions, deletions or additions, relative to the LPA receptor.

It will be apparent to the skilled worker that sequences of the LPA receptor of at least about 15 nucleotides, and preferably of at least about 17 nucleic acids, could be used to generate proves useful to identify nucleic acid molecules encoding LPA receptor encoding vzg-1 homologs. With reference to SEQ ID No. 1 and the nucleotide numbering appearing thereon, such nucleotide fragments include those corresponding in sequence to the transmembrane regions. These sequences, and the intact gene itself, may be used of course to clone vzg-1 related genes by standard hybridization techniques. For example, DNA coding for other vzg-1 receptors, for example other mouse receptor or other mammalian receptors, can be obtained by applying selected techniques of gene isolation or gene synthesis, It is very likely that other species, in particular other mammals including the human encode within their genomes a LPA binding receptor homolog of vzg-1. Isolation of the vzg-1 homolog typically will entail extraction of total messenger RNA from a fresh source of fetal brain tissue, followed by conversion of message to cDNA and formation of a library in for example a bacterial plasmid, more typically a bacteriophage. Such bacteriophage harbouring fragments of the human DNA are typically grown by plating on a lawn of susceptible E. coli bacteria, such that individual phage plaques or colonies can be isolated. The DNA carried by the phage colony is then typically immobilized, on a nitro-cellulose or nylon-based hybridization membrane, and then hybridized, under carefully controlled conditions, to a radioactively (or otherwise) labelled probe sequence to identify the particular phage colony carrying the fragment of DNA of particular interest, in this case a vzg-1 homolog. The phage carrying the particular gene of interest is then purified away from all other phages from the library, in order that the foreign gene may be more easily characterized. Typically, the gene or a portion thereof is subcloned into a plasmidic vector for convenience, especially with respect to the full determination of its DNA sequence. Therefore, having herein provided the mouse LPA receptor, it will be appreciated by one of ordinary skill in the art of molecular biology that the human homolog of the mouse vzg-1gene is available by screening a human embryonic brain cDNA or genomic library by using the mouse vzg-1 gene or fragments thereof as a probe, using standard molecular biological techniques.

In the alternative, nucleic acids homologous with vzg-1 can be sources via available databases that store and allow for searching of sequences electronically. In this regard it has been found that the following genes, of unknown function, have the requisite homologies: the mouse clone Rec1.3 (Genebank accession No. U48235, available Feb. 27, 1996); the bovine clone Rec1.3 (Genebank accession No. U48236, available Feb. 27, 1996) and the human clone Edg-2 (Genebank accession No. Y09479, available Nov. 18, 1996).

As an alternative to obtaining LPA encoding DNA directly as a DNA insert from an available or a constructed cDNA library, in light of the present disclosure it can be synthesized de novo using established techniques of gene synthesis. Because of the length of the LPA receptor-encoding DNA of SEQ ID NO 1, application of automated synthesis may require staged gene construction, in which regions of the gene up to about 300 nucleotides in length are synthesized individually and then ligated in correct succession for final assembly. Individually synthesized gene regions can be amplified by PCR. The application of automated synthesis may typically be applied by synthesizing specific regions or fragments of the gene and ligating them, usually via designed overlaps, in correct succession to form the final gene sequence. In this case, the longer the oligonucleotide building blocks, the fewer will be the ligations needed, resulting in greater ease of assembly.

The application of automated gene synthesis techniques provides an opportunity for generating sequence variants of the naturally occurring LPA receptor encoding genes. It will be appreciated, for example, that polynucleotides coding for the LPA receptor herein described can be generated by substituting synonymous codons for those represented in the naturally occurring polynucleotide sequences herein provided. In addition, polynucleotides coding for synthetic variants of the LPA receptor herein provided can be generated which for example incorporate sing amino acid substitutions, deletions or additions. Since it will be desirable typically to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. in the third intracellular loop i.e. residues 225–255.

Having LPA receptor encoding nucleic acid in hand, LPA receptor can be produced in a number of ways, including in vitro transcription and via incorporation of the DNA into a suitable expression vector and expression in the appropriate host, for example a bacteria such as E. coli, yeast or a mammalian cell. A variety of gene expression systems have been adapted for use with these hosts and are now commercially available, and any one of these systems can be selected to drive expression of the LPA receptor-encoding DNA. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection such as a gene coding for neomycin resistance in which case the transformants are plated in medium supplemented with neomycin.

These systems, available typically in the form of plasmidic vector, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which the receptor-encoding DNA is linked with expression controlling DNA sequences recognized by the host, and which include a region 5' of the receptor-encoding DNA to drive expression, and a 3' region to terminate expression.

Included among the various recombinant DNA expression systems that can be used to achieve mammalian call expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of tetroviruses, insect cell promoters such as those regulated by temperature, and isolated from Drosophila, as well as mammalian gene promoters such as those regulated by heavy metals i.e. the metalothionein gene promoter, and other steroid-inducible promoters.

In another embodiment the invention provides cells or membranes derived therefrom expressing at the cell surface an LPA receptor encoded by a heterologous DNA molecule. For incorporation into cell plasma membranes the vector can be designed to provide a suitable heterologous signal peptide sequence or the naturally occurring signal peptide encoding sequence can be incorporated into the expression vector. Conceivably any may be useful in this regard, provided that the endogenous response, if any, is accounted for. Suitable cells include the mouse cell lines TSM or TR (Chun et al. 1996, Mol. Neurosci. 7, 304–321). Other cell lines which may be used for this purpose and which are currently available include the Chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC-HTB 10) and SK-N-SH (ATCC HTB 11). Such cells or membrane preparations are useful to screen LPA receptor candidate ligands.

For use in screening assays, cell lines expressing the receptor-encoding DNA can be stored frozen for later use. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purpose, i.e., ligand binding experiments, frozen intact cells are homogenized while in cold water suspension and a membrane pellet is collected after centrifugation. The pellet is then washed in cold water, and dialyzed to remove endogenous LPA receptor ligands that would otherwise compete for binding in the assays. The dialyzed membranes may then be used as such, or after storage in lyophilized form, in the ligand binding assays.

The binding of a candidate ligand to a selected LPA receptor of the invention is performed typically using a predetermined amount of cell-derived membrane (measured for example by protein determination), generally from about 25 ug to 100 ug. Generally, competitive binding assays will be useful to evaluate the affinity of a test compound relative to LPA. This competitive binding assay is performed by incubating the membrane preparation with radiolabelled LPA, for example [$^3$H]-LPA, in the presence of unlabelled test compound added at varying concentrations. Following incubation, either displaced or bound radiolabelled LPA can be recovered and measured, to determine the relative binding affinities of the test compound and LPA for the LPA receptor used as substrate. In this way, the affinities of various compounds for the LPA receptor can be measured.

Alternatively, intact, fresh cells, harvested about two days after transient transfection or after about the same period following fresh plating of stably transfected cells, can be used for ligand binding assays by the same methods as used for membrane preparations. In this case, the cells must be harvested by more gentle centrifugation so as not to damage them, and all washing must be done in a buffered medium.

As an alternative to using cells that express receptor-encoding DNA, ligand characterization may also be performed using cells for example *Xenopus ococytes,* that yield functional membrane-bound receptor following introduction of messenger RNA coding for a LPA receptor. In this case, the LPA receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into *Xenopus ococytes.* Each *ococyte* is a single cell, but is large enough to be penetrated by a fine-tipped microneedle without causing irreparable damage. Following the injection of nL volumes of an RNA solution, the *ococytes* are left to incubate for up to several days, whereupon the *ococytes* are tested for the ability to respond to a particular ligand molecule supplied in a bathing solution.

In addition to using the receptor-encoding DNA to construct cell lines usefule for ligand screening, expression of the DNA can according to another aspect of the invention be performed to produce fragments of the receptor in soluble form, for structure investigation, to raise antibodies and for other experimental uses. It is expected that the portion of the LPA receptor responsible for binding a ligand molecule resides on the outside of the cell, i.e., extracellular. It is therefore desirable in the first instance to facilitate the characterization of the receptor-ligand interaction by providing this extracellular ligand-binding domain in quantity and is isolated from, i.e., free from the remainder of the receptor.

To accomplish this, the full-length LPA receptor-encoding DNA may be modified by site-directed mutagenesis, so as to introduce a translational stop codon into the extracellular N-terminal region, immediately before the sequence encoding the first transmembrane domain (TM1), i.e., before residue 47 as shown in SEQ ID No. 2. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf 9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the LPA receptor. *Aspergillus ridulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

The availability of isolated extracellular ligand-binding domains of the receptor protein makes it feasible to determine the 3-dimensional structures of these ligand-binding regions, with or without a candidate ligand complexed thereto, by a combination of X-ray crystallographic and advanced 2D-NMR techniques. In this way, additional new candidate compounds, predicted to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approx. 100–130 amino acids in length, then the powerful technique of 2-D NMR can also be applied to structure determination. This enables not only the determination of the domain structure, but also provides dynamic information about the drug-receptor interaction.

For use particularly in detecting the presence and/or location, for example in brain tissue, the present invention also provides, in another of its aspects, labelled antibody to a LPA receptor. To raise such antibodies, there may be used as immunogen either the intact, soluble receptor or an immunogenic fragment thereof, produced in a microbial or mammalian cell host as described above or by standard peptide synthesis techniques. Regions of the LPA receptor particularly suitable for use as immunogenic fragments include those corresponding in sequence to an extracellular region of the receptor, or a portion of the extracellular region, such as peptides consisting of amino acids 1–36 of SEQ ID No. 1 and peptides corresponding to regions between transmembrane domains thereof such as a peptide consisting of peptides corresponding to amino acids: 105–121; 182–205; 280–290 of SEQ ID No. 2.

The raising of antibodies to the desired LPA receptor or fragment immunogen can be achieved, for polyclonal antibody production as described above or as in Example 4, from the blood of an animal that has been immunized with the immunogen. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using liner technology established for this purpose.

Animal model systems which elucidate the physiological and behavioural roles of the LPA receptor are produced by creating transgenic animals in which the activity of the LPA receptor is either increased or decreased, or the amino acid sequence of the expressed LPA receptor is altered, by a variety of techniques. Examples of those techniques include, but are not limited to: 1) Insertion of normal or mutant versions of DNA encoding a LPA receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these LPA receptor sequences. The technique of homologous recombination is well known in the art. It replaces the native gene with the inserted gene and so is useful for producing an animal that cannot express native LPA receptor but does express, for example, an inserted mutant LPA receptor, which has replaced the native LPA receptor in the animal's genome by recombination, resulting in underexpression of the transporter. Microinjection adds genes to the genome, but does not remove them, and so is useful for producing an animal which expresses its own and added LPA receptorS, resulting in overexpression of the LPA receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a LPA receptor is cesiumchloride purified from a vector by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the transgene. The DNA, in an appropriately buffered solution, is put into a microinjection needle (which may be made from capillary tubing using a piper puller) and the egg to be injected is put in a depression slide. The needle is inserted into the pronucleus of the egg, and the DAN solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only methods for inserting DNA into the egg cell, and is used here only for exemplification purposes.

EXAMPLE 1

Isolation of the LPA receptor (vzg-1)

Poly-A+RNA was isolated from the neocortical murine cells lines TR and TSM cells (Chun and Jaenisch, 1996, Mol. Cell Neurosci. 7:304–321). The RNA was trice selected for poly A+ on oligo-dT cellulose (Pharmacia, Piscataway, N.J.) and 10.5 µg of RNA was reverse transcribed using oligo-dT or random hexamer primers in 50 mM Tris, pH 8.3, 6 mM $MgCl_2$, 40 mM KCl, 1 mM DTT, 1 mM each dNTPs, and 10 U/µl Moloney murine leukemia virus reverse transcriptase (Gibco, Gaithersburg, Md.). RNA and primers were heated to 65° C. (5 min), cooled to RT, additional reagents added, then heated to 37° (2 hr). This cDNA was PCR amplified using a degenerate primer set derived from the conserved regions of transmembrane (TM) domain II and VII of the GPCR family, as follows:

PCR reactions used 40 ng of cDNA in 10 mM Tris, pH 8.3, 50 mM KCl, 2 µM of each primer, 1.5 mM $MgCl_2$, 0.2 µM each dNTPs, and 2.5 U Taq DNA polymerase. All 30 pairwise combinations of primers were used. Reactions were placed in Perkin-Elmer 480 thermal cycler (Applied Biosystems, Foster City, Calif.) at 94° C. (3 min), then cycled 25–40 times at 96° C. (45 sec), 47° C. (144 sec) or 53° C. (216 sec), and 72° C. (3 min, 6 sec extension/cycle). Products were T/A cloned, screened by in situ hybridization and sequenced. One product "513" was localized to the vz. Northern blot analysis of embryonic brain detected a single 3.8 kb transcipt.

The product used to clone vzg-1 ("513") was independently isolated using

TM II primer 5'AA(C/T)T(A/G)(C/G)ATI(A/C)TI(C/G)TIAA(C/T)C/T)TIGCIGTIGCIGA (SEQ ID NO: 3) and TM VII primers 5'CTGI(C/T)(G/T)A/G)TTCATIA(A/T)I(A/C)(A/C)(A/G)TAIA(C/T)IA(C/T)IGG(A/G)TT (SEQ ID NO: 4), 5'TCIAT(A/G)TT(A/G)AAIGTIGT(A/G)TAIATIATIGG(A/G)TT (SEQ ID NO: 5), and 5'AA(A/G)TCIGG(A/G)(C/G)(A/T)ICGI(C/G)A(A/G)TAIAT(C/G)AIIGG(A/G)TT. (SEQ ID NO: 6)

Clone "513" was used to screen 500,000 phage at high stringency from a postnatal day 20 Balb/c mouse brain library (Stratagen, La Jolla, Calif.). Clone "pSt3", containing a 2249 bp insert, was sequenced completely in both directions by the dideoxy chain termination method. This cDNA contains an open reading frame encoding a 41 kD protein with seven hydrophobic membrane spanning domains, as well as other features of the GPCR family. These sequence data were made available Nov. 30, 1996 inGenBank/EMBL/DDBJ under the accession number U70622.

EXAMPLE 2

Morpholigical Assay

Vectors for transfection contained the 1131 bp Ear-I-Nae I vzg-1 open reading flame fragment from SEQ ID No. 2 in the sense or antisense orientation, blunt-end cloned into the EcoRV site of pcDNAI/Amp (Invitrogen, San Diego) by standard protocols.

Neuronal cell line TSM, which has a low expression of endogenous vzg-1 transcript compared to the TR cell line, was transfected both trasiently and stably with expression vectors containing vzg-1 in the sense or antisense orientation. Transient transfection used calcium phosphate precipitation, with 10:1 molar ration of vzg-1 expression plasmid to β-galactosidase expression plasmid pCMVβ (Clonetech, Palo Alto, Calif.). After 18 h, cells were refed, grown for 24 h, then fixed in 4% paraformaldehyde in PBS for 10 min, and stained for β-galactosidase activity. Positive cells (200/plate) were counted "blind." The statistical program Instat (Graphpad, Software, San Diego, Calif.) was used for one way ANOVA and the Student-Newman-Keuls pairwise t-test. Stable transfection used a 10:1 molar ratio of vzg-1 expression plasmid to pSV2-puro. (Vara et al. 1986, Nuc. Acid Res. 14, 4167–4624) and selection in medium containing 10 µg/ml puromycin. After 2 weeks of selection, single colonies of cells were picked using cloning cylinders, expanded, then stored or processed for RNA isolation and northern analyses as previously described, (Chun et al. Supra).

Stable cell lines (5000/well in 24 well plates) were serum-starved for 24 h, then media containing the desired agents was added to the required final concentration. Cells were fixed in 4% paraformaldehyde in PBS to terminate incubation and examined. Experiments were performed in duplicate (200 cells counted/well) and representative samples were evaluated by multiple investigators. Statistical methods used were identical to transient experiments.

Transfection with the vzg-1 sense expression vector induced neurite retraction and cell rounding, which was maintained for at least 24 h "sustained cell rounding". This morphological change required the presence of serum. Sense transfected cells exposed to serum had 48±3.6% round morphology, compared to 22±5.0% without serum.

The reproducibility of cell rounding allowed its use as a bioassay to identify putative ligands for vzg-1. Boiling the serum did not abolish its ability to mediate cell rounding, indicating that the ligand was a heat stable molecule that might be associated with 1) cytoskeletal changes and 2) cell proliferation, since vzg-1 expression was restricted to the vz. A molecule present in serum that met these criteria was LPA. Since endogenous vzg-1 should be active in the cell lines from which it was identified, untransfected TSM cells were first assayed for their ability to respond to LPA (Avanti Polar Lipids (Alabaster, Ala.), all lipids were synthetic, 89–99% pure). TSM cells responded with a rapid increase in the percentage of round cells. However, this response was reversible such that by 3 h the percentages of round cells returned to their baseline values.

Transfection of TSM cells with vzg-1 in the sense orientation sustained the rounding response to LPA such that at 3 h 49±4.9% of treated transfected cells still displayed a round morphology, compared to 29±1.9% of untreated transfected cells. Importantly, thrombin, a serum component which also induces cell rounding in some neural cell lines did not induce sustained cell rounding in cells transfected with vzg-1, although it did induce sustained cell rounding in cells transfected with the thrombin receptor. Thus, transient overexpression of vzg-1 specifically alters LPA-mediated changes in cell morphology.

EXAMPLE 3

Membrane Isolation and Ligand Binding Assay

Cell lines were grown in 90% confluence, washed with PBS, scraped from the plate, centrifuged for 5 min (110×g), washed with PBS, re-centrifuged, and the pellet then resuspended 10 ml of ice cold 20 mM Tris, pH 7.5, disrupted by twenty strokes in a glass homogenizer, and sonicated on ice with three 10 s bursts using a micro-ultrasonic cell disrupter (Kontes Glass, Hayward, Calif.). After low speed centrifugation (1000×g, 15 min, 4° C.), membranes were pelleted from the supernatant (16000×g, 30 min, 4° C.) and resuspended at 3 µg/ul, protein in ice cold 20 mM Tris, pH 7.5. Just prior to analysis, membranes were re-sonicated for 5 s on ice until the solution became transparent, then LPA binding assays carried out as previously described, (Thompson et al. Mol. Pharmacol. 45, 718–723). Briefly, binding reactions (500 µg/ml membrane protein in an assay buffer of 20 mM Tris, pH 7.5 and 0.5 mM $CuSO_4$) were initiated by addition of 1-oleoyl-(9,10-$^3$H)-LPA (56.2 Cl/mmol) (DupontHEN, Boston, Mass.) to a final concentration of 8.5 nM (230,000 CPM) and incubated (30° C., 30 min). To assess nonspecific binding, 2 µM unlabeled 1-oleoyl-LPA was added to a set of parallel reactions. Reactions ere run through PD-10 Sephadex G25M columns (Pharmacia, Piscataway, N.J.) to separate bound from free ligand. The eluent (1.5 ml) was mixed with scintillation fluid (Ultima Gold; Packard Instument Co., Meriden, Conn.) and counted at RT. About 5–10% of the total input CPM were collected in the eluent. Uncorrected total binding ranged from 13,000 to 20,000 CPM. Because LPA forms aggregates that are excluded from the column bed and thus collected in the eluent, each experiment was performed in parallel using reactions without membranes, in the presence or absence of 2 µM LPA, to determine eluted background CPM. Total and non-specific CPM were corrected by subtraction of the appropriate background CPM. Specific CPM were calculated by subtracting corrected non-specific CPM from corrected total CPM. Overall, with correction, non-specific CPM were 61% of total CPM. Experiments were done in triplicate and the results statistically analyzed using Student's t-test.

EXAMPLE 4

Production of polyclonal antisera to the LPA receptor

A rabbit polyclonal antiserum was raised against Vzg-1 by cDNA vaccination according to the method of Donnelly et al., J. Infect. Dis. 1996, 173:314–320 and Raz et al., PNAS USA 1994, 91:9519–9523. Briefly, Twice weekly intradermal injections of vzg-1 expression construct (20 µg) in PBS for 6 weeks were followed by a week hiatus, then injections repeated for 4 weeks and serum collected. Antiserum was collected, diluted in appropriate buffers and screened by Westeryl blot anaysis. The antiserum recognizes an approximately 41 kd protein in brain and cell line extracts that is absent from pre-immune controls.

```
        GAATTCGGCA CGAGGCACAG TGCTGCCCTC CGTAGGCTCC GGGTTGTGCT GGGGTGAGGC
     61 TTGGGTTGGG TTGGCCCGGC GGCTGCGTGA ACTGCGGAGC TGGACCTAGC AGGCTTACAG
    121 TICCTCCTAG CATGACCGAG ATCTGATCAG CCAACCCGCG CATTGCTTTT TGTGCCTGGC
    181 ACTGCAGTGC AGGGGGCCTC TTCATCGCCC CAAACTACAG CACTGTCATG GCAGCTGCCT
    241 CTACTTCCAG CCCTGTAATT TCACAGCCCC AGTTCACAGC CATGAACGAA CAACAGTGCT
    301 TCTACAATGA GTCTATCGCC TTCTTTTATA ACCGGAGTGG GAAATATCTA GCCACAGAAT
    361 GGAACACAGT GAGCAAGCTG GTGATGGGAC TGGGCATCAC TGTTTGCGTG TTCATCATGT
    421 TGGCCAATCT CCTGGTCATG GTGGCAATCT ACGTCAACCG CCGCTTCCAT TTCCCTATTT
    481 ATTACTTGAT GGCCAACCTG GCTGCTGCAG ACTTCTTCGC TGGATTGGCC TACTTCTACC
    541 TGATGTTCAA TACAGGACCT AATACCCGGA GACTGACTGT TAGCACGTGG CTCCTCCGGC
    601 AGGGCCTCAT TGACACCAGC CTGACAGCTT CTGTGGCCAA CCTGCTGGCT ATTGCTATCG
    661 AGAGGCACAT CACGGTTTTC CGCATGCAGC TCCATACACG AATGAGCAAC CGGCGCGTGG
    721 TGGTGGTGAT TGTAGTCATC TGGACTATGG CCATTGTGAT GGGTGCTATA CCCAGTGTGG
    781 GCTGGAACTG CATCTGTGAT ATCGATCACT GTTCCAACAT GGCACCCCTC TACAGTGACT
    841 CCTACTTAGT CTTCTGGGCC ATTTTCAACC TGGTGACCTT TGTGGTCATG GTGGTTCTCT
    901 ACGCTCACAT CTTTGGCTAT GTTCGCCAGA GGACTATGAG GATGTCTCGG CATAGTTCTG
    961 GACCCAGGAG GAATCGGGAC ACCATGATGA GCCTTCTGAA GACTGTGGTC ATTGTGCTTG
   1021 GTGCCTTTAT TGTCTGCTGG ACTCCGGGAT TGGTCTTGTT ATTGCTGGAT GTGTGCTGCC
```

-continued

```
1081 CGCAGTGCGA TGTCCTGGCC TATGAGAAGT TCTTCCTCCT CCTGGCCGAG TTCAACTCTG
1141 CTATGAACCC CATCATCTAC TCCTACCGCG ACAAAGAGAT GAGCGCCACC TTCAGGCAGA
1201 TCCTGTGTTG CCAGCGCAAC GAGAACCCTA ATGGCCCCAC GGAAGGCTCT GACCGCTCTG
1261 CCTCCTCCCT CAACCACACC ATTCTGGCTG GAGTTCACAG CAACGACCAC TCTGTGGTTT
1321 AGAAGGAAGC CAGCCGGCCT CTGTGGATCT GTGAACCCCA CCCTACCCCC CATTGCCAGG
1381 GCAAGGTGGG GAGCCAGAGG AGATGAGGAC ACTCCTGTAC TTAACACTAA CCAATGGCAG
1441 TATTTGTCCC TAGACCCAAG AGACTTGAGG ATGAATTTAT TTGGCAGGCC CCATCTTCTC
1501 CTTTGGAAAA CAGAAGGGGA CCGTCTTGTG GTGGAATTGA GAAATGGACT CTGGGGTGAC
1561 CGTGTAGCAT TCACTAACTA GACTTAAAAG ATTTTATGTG GTTTGGCTTA AGCCAGGAAA
1621 AAAAAATCTG CTGAATTGAG TATACAATCG AGTATACACA GGCTTCCCCT TTAAAGAACA
1681 AACAATACAT TGCATTTATT AATGAGTATG TTTATGCCTG ACAGCATGTT TGTGATCGAA
1741 AAGACTGCTA AACTGACATA GATGAGTTGT TTTTTTTTTT TTGTTTTTTG TTTTTTTTA
1801 CATGATGGAG GAAAAGTATA AATTAGAATG ATTTTGTGT TTGTTTAGAA AGCAAGCATG
1861 TGGTGTGTGT ATTCAGTATG CCTTTCTTTA AAGATAAAAG GCCACTATTT TAAATCTTCT
1921 AGGGAATAGA AGAATCTAGT AAAAACCAGT ATTCATTTAG GCTACAGGAA AAACCATATC
1981 CTAATCAATT ACCTTTTAAT TAAAGTAATG AAATATACAT GAAAGGCAAA GTAATGTGAG
2041 CTTGTCACCC AAAGAGTGTG TGCTCTCCAA ACGCTGGAGG AGATGAAGCT GTAGCGTTGT
2101 CCCTGCATAG TGAAGATACC CACGTGCGTT CTCAGTGCCA GACCCTCAGT GGGACTTGTT
2161 TTAAAGCCTG TGGTTTTCCA AGTTAGAAAA TAATACCTAC TTACTATAGA AAACTTGAAA
2221 ATTGCAGAAC TGTGTGAAAA AAAAAAAAA
```

SEQ ID No. 1

```
  1  M A A A S T S S P V I S Q P Q F T A M N E Q Q C F Y N E S I A F F
                                              TM I
 34  Y N R S G K Y L A T E W N T V S K L V M G L G I T V C V F I M L A
                                      TM II
 67  N L L V M V A I Y V N R R F H F P I Y Y K M A N L A A A D F F A G
                                      TM III
100  L A Y F Y L M F N T G P N T R R L T V S T W L L R Q G L I D T S L
                                              TM IV
133  T A S V A N L L A I A I E R H I T V F R M Q L H T R M S N R R V V
166  V V I V V I W T M A I V M G A I P S V G W N C I C D I D H C S N M
                      TM V
199  A P L Y S D S Y L V F W A I F N L V T F V V M V V L Y A H I F G Y
                                              TM VI
232  V R Q R T M R M S R H S S G P R R N R D T M M S L L K T V V I V L
                                              TM VII
265  G A F I V C W T P G L V L L L L D V C C P Q C D V L A Y E K F F L
298  L L A E F N S A M N P I I Y S Y R D K E M S A T F R Q I L C C Q R
331  N E N P N G P T E G S D R S A S S L N H T I L A G V H S N D H S V V
```

SEQ ID No. 2

---

We claim:

1. An isolated nucleic acid encoding a lysophosphatidic acid receptor comprising the amino acid sequence set forth in SEQ ID NO: 2.

2. The nucleic acid of claim 1, wherein the nucleic acid is cDNA.

3. The complement of the isolated nucleic acid of claim 1.

4. A recombinant DNA molecule, comprising a DNA sequence encoding a lysophosphatidic acid receptor comprising the amino acid sequence set forth in SEQ ID NO: 2, and expression controlling elements linked operably with the DNA sequence to drive expression thereof.

5. The recombinant DNA molecule of claim 4, wherein the DNA sequence is a cDNA sequence.

6. The recombinant DNA molecule of claim 4, wherein the expression controlling elements drive expression of the DNA sequence in a mammalian cell.

7. A cell comprising the recombinant DNA molecule of claim 4.

8. The cell of claim 7, wherein the cell is a mammalian cell.

9. A method of identifying a lysophosphatidic acid receptor ligand, comprising (a) providing a substrate selected from the group consisting of (1) a cell that produces a lysophosphatidic acid receptor comprising the amino acid sequence set forth in SEQ ID NO: 2, and (2) a membrane preparation obtained from said cell;

(b) incubating said substrate with a test ligand, and thereafter (c) determining any binding between the lysophosphatidic acid receptor and said test ligand.

10. The method of claim 9, wherein the substrate is a cell that produces a lysophosphatidic acid receptor comprising the amino acid sequence set forth in SEQ ID NO: 2.

11. The method of claim 10, wherein the cell is mammalian cell.

12. The method of claim 11, wherein the call comprises a recombinant DNA molecule comprising a DNA sequence encoding said receptor operably linked to expression controlling elements such that said receptor is expressed on the cell.

13. The method of claim 11, wherein the cell is a cell that responds to lysophosphatidic acid by cell rounding.

14. The method of claim 13, wherein binding between the lysophosphatidic acid receptor and the test ligand is determined by determining any call rounding.

15. A method of identifying a lysophosphatidic acid receptor ligand, comprising (a) providing a substrate selected from the group consisting of (1) a cell that produces a lysophosphatidic acid receptor comprising the amino acid sequence set forth in SEQ ID NO: 2, and )2) a membrane preparation obtained from said cell;

(b) incubating said substrate with (1) a reference ligand comprising lysophosphatidic acid, and (2) a test ligand; and thereafter (c) determining any binding between the lysophosphatidic acid receptor and the test ligand by determining whether the test ligand modulates binding of the lysophosphatidic acid receptor with the reference ligand.

16. The method of claim 15, wherein the substrate is a cell that produces a lysophosphatidic acid receptor comprising the amino acid sequence set forth in SEQ ID No: 2.

17. The method of claim 16, wherein the cell is a mammalian cell.

18. The method of claim 17, wherein the cell comprises a recombinant DNA molecule comprising a DNA sequence encoding said receptor operably linked to expression controlling elements such that said receptor is expressed on the cell.

19. The method of claim 17, wherein the cell is a cell that responds to lysophosphatidic acid by cell rounding.

20. The method of claim 19, wherein binding between the lysophosphatidic acid receptor and the test ligand is determined by determining any cell rounding.

21. The method according to claim 15, wherein substrate is incubated first with a reference ligand comprising detectably labeled lysophosphatidic acid, and thereafter with a test ligand.

22. The method of claim 21, wherein any binding between the lysophosphatidic acid receptor and the test ligand is determined by measuring displacement of the detectably labeled lysophosphatidic acid receptor.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 2250 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GAATTCGGCA CGAGGCACAG TGCTGCCCTC CGTAGGCTCC GGGTTGTGCT GGGGTGAGGC      60

TTGGGTTGGG TTGGCCCGGC GGCTGCGTGA ACTGCGGAGC TGGACCTAGC AGGCTTACAG     120

TTCCTCCTAG CATGACCGAG ATCTGATCAG CCAACCCGCG CATTGCTTTT TGTGCCTGGC     180

ACTGCAGTGC AGGGGGCCTC TTCATCGCCC CAAACTACAG CACTGTCATG GCAGCTGCCT     240

CTACTTCCAG CCCTGTAATT TCACAGCCCC AGTTCACAGC CATGAACGAA CAACAGTGCT     300

TCTACAATGA GTCTATCGCC TTCTTTTATA ACCGGAGTGG GAAATATCTA GCCACAGAAT     360

GGAACACAGT GAGCAAGCTG GTGATGGGAC TGGGCATCAC TGTTTGCGTG TTCATCATGT     420

TGGCCAATCT CCTGGTCATG GTGGCAATCT ACGTCAACCG CCGCTTCCAT TTCCCTATTT     480

ATTACTTGAT GGCCAACCTG GCTGCTGCAG ACTTCTTCGC TGGATTGGCC TACTTCTACC     540

TGATGTTCAA TACAGGACCT AATACCCGGA GACTGACTGT TAGCACGTGG CTCCTCCGGC     600

AGGGCCTCAT TGACACCAGC CTGACAGCTT CTGTGGCCAA CCTGCTGGCT ATTGCTATCG     660

AGAGGCACAT CACGGTTTTC CGCATGCAGC TCCATACACG AATGAGCAAC CGGCGCGTGG     720

TGGTGGTGAT TGTAGTCATC TGGACTATGG CCATTGTGAT GGGTGCTATA CCCAGTGTGG     780

GCTGGAACTG CATCTGTGAT ATCGATCACT GTTCCAACAT GGCACCCCTC TACAGTGACT     840

CCTACTTAGT CTTCTGGGCC ATTTTCAACC TGGTGACCTT TGTGGTCATG GTGGTTCTCT     900

ACGCTCACAT CTTTGGCTAT GTTCGCCAGA GGACTATGAG GATGTCTCGG CATAGTTCTG     960

GACCCAGGAG GAATCGGGAC ACCATGATGA GCCTTCTGAA GACTGTGGTC ATTGTGCTTG    1020

GTGCCTTTAT TGTCTGCTGG ACTCCGGGAT TGGTCTTGTT ATTGCTGGAT GTGTGCTGCC    1080

CGCAGTGCGA TGTCCTGGCC TATGAGAAGT TCTTCCTCCT CCTGGCCGAG TTCAACTCTG    1140

CTATGAACCC CATCATCTAC TCCTACCGCG ACAAAGAGAT GAGCGCCACC TTCAGGCAGA    1200

TCCTGTGTTG CCAGCGCAAC GAGAACCCTA ATGGCCCCAC GGAAGGCTCT GACCGCTCTG    1260

CCTCCTCCCT CAACCACACC ATTCTGGCTG GAGTTCACAG CAACGACCAC TCTGTGGTTT    1320

AGAAGGAAGC CAGCCGGCCT CTGTGGATCT GTGAACCCCA CCCTACCCCC CATTGCCAGG    1380

GCAAGGTGGG GAGCCAGAGG AGATGAGGAC ACTCCTGTAC TTAACACTAA CCAATGGCAG    1440

TATTTGTCCC TAGACCCAAG AGACTTGAGG ATGAATTTAT TTGGCAGGCC CCATCTTCTC    1500

CTTTGGAAAA CAGAAGGGGA CCGTCTTGTG GTGGAATTGA GAAATGGACT CTGGGGTGAC    1560

CGTGTAGCAT TCACTAACTA GACTTAAAAG ATTTTATGTG GTTTGGCTTA AGCCAGGAAA    1620

AAAAAATCTG CTGAATTGAG TATACAATCG AGTATACACA GGCTTCCCCT TTAAAGAACA    1680

AACAATACAT TGCATTTATT AATGAGTATG TTTATGCCTG ACAGCATGTT TGTGATCGAA    1740
```

-continued

```
AAGACTGCTA AACTGACATA GATGAGTTGT TTTTTTTTTT TTGTTTTTTG TTTTTTTTTA    1800

CATGATGGAG GAAAAGTATA AATTAGAATG ATTTTTGTGT TTGTTTAGAA AGCAAGCATG    1860

TGGTGTGTGT ATTCAGTATG CCTTTCTTTA AAGATAAAAG GCCACTATTT TAAATCTTCT    1920

AGGGAATAGA AGAATCTAGT AAAAACCAGT ATTCATTTAG GCTACAGGAA AAACCATATC    1980

CTAATCAATT ACCTTTTAAT TAAAGTAATG AAATATACAT GAAAGGCAAA GTAATGTGAG    2040

CTTGTCACCC AAAGAGTGTG TGCTCTCCAA ACGCTGGAGG AGATGAAGCT GTAGCGTTGT    2100

CCCTGCATAG TGAAGATACC CACGTGCGTT CTCAGTGCCA GACCCTCAGT GGGACTTGTT    2160

TTAAAGCCTG TGGTTTTCCA AGTTAGAAAA TAATACCTAC TTACTATAGA AAACTTGAAA    2220

ATTGCAGAAC TGTGTGAAAA AAAAAAAAAA                                    2250
```

(2) INFORMATION FOR SEQ ID NO:2:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Ala Ala Ala Ser Thr Ser Ser Pro Val Ile Ser Gln Pro Gln Phe
  1               5                  10                  15

Thr Ala Met Asn Glu Gln Gln Cys Phe Tyr Asn Glu Ser Ile Ala Phe
             20                  25                  30

Phe Tyr Asn Arg Ser Gly Lys Tyr Leu Ala Thr Glu Trp Asn Thr Val
         35                  40                  45

Ser Lys Leu Val Met Gly Leu Gly Ile Thr Val Cys Val Phe Ile Met
 50                  55                  60

Leu Ala Asn Leu Leu Val Met Val Ala Ile Tyr Val Asn Arg Arg Phe
 65                  70                  75                  80

His Phe Pro Ile Tyr Tyr Leu Met Ala Asn Leu Ala Ala Ala Asp Phe
                 85                  90                  95

Phe Ala Gly Leu Ala Tyr Phe Tyr Leu Met Phe Asn Thr Gly Pro Asn
                100                 105                 110

Thr Arg Arg Leu Thr Val Ser Thr Trp Leu Leu Arg Gln Gly Leu Ile
            115                 120                 125

Asp Thr Ser Leu Thr Ala Ser Val Ala Asn Leu Leu Ala Ile Ala Ile
130                 135                 140

Glu Arg His Ile Thr Val Phe Arg Met Gln Leu His Thr Arg Met Ser
145                 150                 155                 160

Asn Arg Arg Val Val Val Val Ile Val Val Ile Trp Thr Met Ala Ile
                165                 170                 175

Val Met Gly Ala Ile Pro Ser Val Gly Trp Asn Cys Ile Cys Asp Ile
                180                 185                 190

Asp His Cys Ser Asn Met Ala Pro Leu Tyr Ser Asp Ser Tyr Leu Val
            195                 200                 205

Phe Trp Ala Ile Phe Asn Leu Val Thr Phe Val Val Met Val Val Leu
210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
                245                 250                 255
```

```
Leu Lys Thr Val Val Ile Val Leu Gly Ala Phe Ile Val Cys Trp Thr
            260                 265                 270

Pro Gly Leu Val Leu Leu Leu Asp Val Cys Cys Pro Gln Cys Asp
        275                 280                 285

Val Leu Ala Tyr Glu Lys Phe Phe Leu Leu Leu Ala Glu Phe Asn Ser
    290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Asn Glu Asn Pro Asn Gly
                325                 330                 335

Pro Thr Glu Gly Ser Asp Arg Ser Ala Ser Ser Leu Asn His Thr Ile
            340                 345                 350

Leu Ala Gly Val His Ser Asn Asp His Ser Val Val
            355                 360
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 9..30
        (D) OTHER INFORMATION: /note= "N represents "I" for the
            nucleotide Inosine which will pair with any of
            A, G, C and T."

(xi) SEQUENCE DESCRIPTION: SEQ ID NO:3:

AAYTRSATNM TNSTNAAYYT NGCNGTNGCN GA                          32

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 4..28
        (D) OTHER INFORMATION: /note="N represents "I" for the
            nucleotide Inosine which will pair with any of
            A, G, C and T."

(xi) SEQUENCE DESCRIPTION: SEQ ID NO:4:

CTGNYKRTTC ATNAWNMMRT ANAYNAYNGG RTT                        33

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature

```
        (B) LOCATION: 3..27
        (D) OTHER INFORMATION: /note= "N represents "I" for the
            nucleotide Inosine which will pair with any of A, G,
            C and T."

(xi) SEQUENCE DESCRIPTION: SEQ ID NO:5:

TCNATRTTRA ANGTNGTRTA NATNATNGGR TT                                       32

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 6..27
        (D) OTHER INFORMATION: /note= "N represents "I" for the
            nucleotide Inosine which will pair with any of A, G, C
            and T."

(xi) SEQUENCE DESCRIPTION: SEQ ID NO:6:

AARTCNGGRS WNCGNSARTA NATSANNGGR TT                                       32
```